United States Patent
Lindner et al.

(10) Patent No.: US 9,649,856 B2
(45) Date of Patent: May 16, 2017

(54) METHOD AND DEVICE FOR INSPECTING OR CORRECTING A DIRECT PRINT ON CONTAINERS WITH A RELIEF-LIKE SURFACE CONTOUR

(71) Applicant: KRONES AG, Neutraubling (DE)

(72) Inventors: Peter Lindner, Langquaid (DE); Frank Winzinger, Regensburg (DE); Sabine Grosch, Ensdorf (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 14/404,107

(22) PCT Filed: Apr. 30, 2013

(86) PCT No.: PCT/EP2013/058993
§ 371 (c)(1),
(2) Date: Nov. 26, 2014

(87) PCT Pub. No.: WO2013/178418
PCT Pub. Date: Dec. 5, 2013

(65) Prior Publication Data
US 2015/0138295 A1 May 21, 2015

(30) Foreign Application Priority Data
Jun. 1, 2012 (DE) .......... 10 2012 209 305

(51) Int. Cl.
*B41M 1/40* (2006.01)
*B41J 3/407* (2006.01)
(Continued)

(52) U.S. Cl.
CPC .............. *B41J 3/4073* (2013.01); *B41M 1/40* (2013.01); *B41J 25/308* (2013.01); *G01N 21/909* (2013.01); *G01N 21/9045* (2013.01)

(58) Field of Classification Search
CPC ..... B41J 3/4073; B41J 25/308–25/3088; B41J 11/002; B41J 3/543; B41M 1/40; B41M 5/0082–5/0094; B41F 17/18
(Continued)

(56) References Cited

U.S. PATENT DOCUMENTS 5,040,459 A * 8/1991 Rambausek ............ B41F 31/04
101/217
7,428,869 B2 * 9/2008 Lutz .............................. 101/483
(Continued)

FOREIGN PATENT DOCUMENTS

| CN | 102431289 | 5/2012 |
|---|---|---|
| DE | 10327628 A1 | 11/2004 |

(Continued)

OTHER PUBLICATIONS

International Search Report for International Application No. PCT/EP2013/058993, dated Oct. 22, 2013.
(Continued)

*Primary Examiner* — Manish S Shah
*Assistant Examiner* — Yaovi M Ameh
(74) *Attorney, Agent, or Firm* — Marshall, Gerstein & Borun LLP

(57) ABSTRACT

Method for inspecting a direct print on containers with a relief-like surface contour, where the relief-like surface contour is at least partially printed onto, the direct print applied onto the relief-like surface contour is, with an inspection device, inspected in terms of its quality and/or position.

19 Claims, 7 Drawing Sheets

(51) Int. Cl.
*B41J 25/308* (2006.01)
*G01N 21/90* (2006.01)

(58) Field of Classification Search
USPC .................................. 347/2, 4, 8, 101, 110
See application file for complete search history.

(56) References Cited

U.S. PATENT DOCUMENTS

| | | | |
|---|---|---|---|
| 7,565,961 B2* | 7/2009 | Fiegler | B65G 29/00 |
| | | | 198/459.2 |
| 8,667,895 B2* | 3/2014 | Gerigk et al. | 101/35 |
| 9,032,872 B2* | 5/2015 | Uptergrove | 101/38.1 |
| 2001/0015407 A1* | 8/2001 | Tsujii | G06T 5/008 |
| | | | 250/252.1 |
| 2006/0243699 A1 | 11/2006 | Smith | |
| 2009/0169719 A1* | 7/2009 | Orr | B41J 3/4073 |
| | | | 427/8 |
| 2010/0110197 A1* | 5/2010 | Lindner | B65C 9/40 |
| | | | 348/161 |
| 2011/0132916 A1 | 6/2011 | Uptergrove et al. | |
| 2012/0199021 A1* | 8/2012 | Till | B41J 3/4073 |
| | | | 101/36 |

FOREIGN PATENT DOCUMENTS

| | | |
|---|---|---|
| JP | 2007008110 A | 1/2007 |
| JP | 2008089379 A | 4/2008 |
| WO | WO-03002349 A2 | 1/2003 |
| WO | WO-03/106177 A2 | 12/2003 |
| WO | WO-2010/034375 A1 | 4/2010 |
| WO | WO-2011009536 A1 | 1/2011 |

OTHER PUBLICATIONS

Second Office Action received in counterpart Chinese patent Application No. 201380028930.1 dated Mar. 9, 2016.
Third Office Action received in counterpart Chinese patent Application No. 201380028930.1 dated Sep. 2, 2016.

* cited by examiner

METHOD AND DEVICE FOR INSPECTING OR CORRECTING A DIRECT PRINT ON CONTAINERS WITH A RELIEF-LIKE SURFACE CONTOUR

CROSS-REFERENCE TO RELATED APPLICATION

The present application is the US national phase of International Patent Application No. PCT/EP2013/058993, filed Apr. 30, 2013, which application claims priority to German Application No. 102012209305.2, filed Jun. 1, 2012. The priority application, DE 102012209305.2, is hereby incorporated by reference.

FIELD OF THE DISCLOSURE

The invention relates to a method and a device for inspecting or correcting a direct print on containers with a relief-like surface contour.

BACKGROUND

It is known to provide packaging containers for products such as beverages, hygiene articles and the like, with relief-like surface contours in the side wall region for achieving high-quality product presentation and/or improved handling. This can in particular with plastic containers contribute to stiffening the container wall as well as enhancing the appearance and the feel of the container. Added value for the container can in general thereby be achieved by a relief-like surface contour, for example, an ornamental structure.

Furthermore, containers are known to be printed onto for the purpose of labeling and/or ornamenting, for example, with characters, logos, patterns and coloring. For this purpose, for example, WO 03/002349 A2 discloses a method for ink-jet printing onto substantially cylindrical container side walls. Methods are also known according to which the relief-like surface contour of a container is printed onto using a direct printing method. For example, the relief-like surface contours, differing from the cylindrical shape of the container side walls, are there printed onto by use of an ink-jet printing process. The surface portions that are slanted relative to the cylindrical shape are there provided with the direct print.

The drawback here is that even small changes in position of the container relative to the print head result in significant deterioration of the print result. For example, a kind of double image is created when the direct print is shifted relative to the relief-like surface contour. The value of the container and therefore also the value of the product contained therein is thereby reduced.

SUMMARY OF THE DISCLOSURE

The object of the present invention is to provide methods and devices that prevent reduction of the value of containers due to inaccurate printing.

The invention satisfies this object with a method for inspecting a direct print on containers with a relief-like surface contour according to which the direct print applied onto the relief-like surface contour inspected is in terms of its quality and/or position, inspected, with an inspection device.

Due to the fact that the direct print applied onto the relief-like surface contour is inspected, in terms of its quality and/or position, with an inspection device, it is possible to sort out the inaccurately printed containers prior to further processing in subsequent processing steps. Such inaccurately printed containers can therefore be recycled very inexpensively and be returned to the production cycleDue to the inspection process by the inspection device likewise possible to draw conclusions from the result about the calibration of the direct printing device and to either recalibrate the latter or to initiate servicing of the direct printing device. This prevents subsequent containers from being inaccurately printed onto and having their value be reduced.

The containers can be filled with beverages, hygiene products, pastes, chemical, biological and/or pharmaceutical products. The method can be applied in particular in a beverage processing plant. The containers can in particular comprise plastic bottles, glass bottles and/or cans. The method for inspecting a direct print on containers with a relief-like surface contour can be used for inspecting a continuous flow of containers.

The relief-like surface contour can be a three-dimensional structure that stands out against a surrounding wall portion by elevations and/or depressions that are selectively and/or reproducibly creatable. Such relief-like surface contours preferably comprise contours at the macroscopic level, which can both be felt as well as seen by the human eye or spatially resolved at the viewing distances that are customary for the use or the sale of the containers.

The direct printing method can be an ink-jet printing process. Inks can in particular be used in the direct printing method that cures with heat or light, in particular, UV-light.

Quality can be understood to be the resolution, the color thickness, the ink thickness and/or the color fidelity of the direct print.

Contour characteristics of the relief-like surface contour and/or printing characteristics of the direct print can with the disclosed method be detected and correlated in the inspection device. By having, firstly, the contour characteristics of the relief-like surface contour and, secondly, the printing characteristics of the direct print be detected, they can with a calculation method be made to match and be correlated. The quality and/or position of the direct print applied onto the relief-like surface contour can thereby be determined more accurately. The relief-like surface contour can be detected with an illuminated screen having regions of different luminance, with a projector for projecting a pattern, and/or with a camera. The relief-like surface contour can also be detected with a 3D-measuring sensor for surface measurement, in particular with a triangulation sensor. The direct print applied can be detected with a camera. Characteristic points and/or lengths can be extracted by use of calculation methods as contour characteristics of the relief-like surface contour and/or as printing characteristics of the direct print which are in particular rotationally invariant.

The containers can prior to printing be attached in a fixed position to holding devices, where in particular the contour characteristics of the relief-like surface contour are detected prior to printing and the printing characteristics are detected after printing. With this procedure, the contour characteristics of the relief-like surface contour can be passed to the direct printing device and used by the latter for aligning the print heads relative to the container. Printing onto the containers can thereby be performed individually more accurately. Due to the fact that the containers are attached to holding devices in a fixed position, the printing characteristics can be detected after printing without again detecting the relief-like surface contour.

The direct print can in this method after inspection additionally be corrected with a correction print. This allows for reduction of container rejects. The direct print can with the correction print be corrected such that the desired print result is obtained. For example, non-printed areas of the relief-like surface contour, due to the failure of a print nozzle, can therewith be corrected.

A correction signal can, with the method disclosed herein, also be transmitted from the inspection device to the direct printing device for calibration of the direct print. This allows for improvement or elimination of systematic print errors. For example, systematic misalignment of the container relative to the direct printing device can thus be recognized and corrected. A statistic analysis of several inspection procedures can occur. In particular, a rotation angle versus time profile of a regulation for moving the holding devices can be calibrated with the correction signal. A regulation of the print nozzles with respect to the ink ejection quantity, ejection timing and/or ejection clocking can be calibrated with the correction signal. In addition, a regulation of the position and alignment of the print heads can with the correction signal be calibrated, in particular by up to six axes.

A further correction signal can in the method be transmitted to a container fabrication machine for its inspecting which is disposed upstream of the inspection device, in particular to a rotary stretch blowing machine. The quality of the containers, in particular of the surface contour, can thereby be improved. The further correction signal can there be used in particular to calibrate parameters of the container fabrication machine. The parameters can be in particular a pre-blowing pressure, a final blowing pressure, a stretching speed, start and finish times of these processes, a temperature profile of a preform, a feed force and/or pressure of a pressure pad. The parameters can there be individually assigned to a blowing station. If, for example, it is recognized that contours of a bottle were formed too weak, then the final blowing pressure of the blow molding machine can be raised by a predetermined or calculated value. If it is recognized that the separation seam on the container is too thick, then the pressure in the pressure pad can be raised for the next containers. For example, the pre-blowing pressure or a heating profile can also be changed when the container exhibits sectional wall thickness variations.

The direct print can with the method also be performed sequentially by print heads with different printing inks and an intermediate result of the direct print can be inspected between at least two print heads and/or the overall result be inspected after printing all printing inks. It can thereby be prevented that a container is printed onto with a first ink with poor quality and is subsequently printed onto with further printing inks. This reduces ink consumption.

In the method, partial surfaces of the relief-like surface contour with a tangent that is slanted relative to the basic shape of the container can be aligned perpendicular to an inspection axis. These partial surfaces can thereby be better detected by the inspection device. The inspection axis can be a camera axis. The tangents can cut the basic shape of the container twice. Such an alignment can also be used during printing itself in order to achieve a better print result.

The invention further provides a device for performing a method for inspecting a direct print on containers with a relief-like surface contour, according to which the device comprises a direct printing device for at least partial printing onto the relief-like surface contour, characterized in that the device comprises at least one inspection device for inspecting the direct print in terms of its quality and/or position.

It can be assessed with the inspection device for inspecting the direct print in terms of its quality and/or position whether the direct print on the containers would reduce the value. When poor print quality is given, the container can then be corrected or sorted out.

The inspection device can comprise a detection unit for relief-like surface contours and/or a triangulation unit. This allows 3D-coordinates of the surface contour to be recognized or determined. The detection unit can comprise an illuminated screen having regions of different luminance, a projector for projecting a pattern, a laser and/or a camera. The inspection device can comprise in particular a calculation unit which is adapted to determine the contour characteristics of the relief-like surface contour from measured data. The inspection device can also comprise a wall thickness measuring device for the container wall thickness.

The device can further comprise an inspection device having at least one camera, where the camera is in particular adapted to detect printing characteristics of the direct print and/or contour characteristics of the relief-like surface contour. These printing characteristics and/or contour characteristics can therewith be recognized in a particularly simple and contactless manner. The inspection device can comprise a calculation unit for image processing. The calculation unit for image processing can in particular be provided for detecting characteristic points and/or lengths of the contour characteristics and/or printing characteristics.

The containers, the direct printing device and/or the inspection device can in the device be arranged pivotably. The direct printing device and/or the inspection device can thereby be aligned at an optimum angle relative to the containers and their relief-like surface contour. A pivot mechanism can be provided to align the direct printing device and/or the inspection device perpendicular to the local profile of the relief-like surface contour. At least one motor in connection with a controller can there be provided to pivot the containers, the direct printing device, and/or the inspection device.

The device can also comprise a correction printing device comprising in particular correction print heads. The correction print heads can comprise actuators for positioning and/or aligning which are in particular connected to a controller. The actuators can comprise at least one electric motor which is particularly adapted to move the correction print heads about a plurality of axes. The controller can be electrically connected to the inspection device.

Furthermore, the inspection device can comprise at least one layer thickness measuring device which is in particular adapted to measure the thickness of at least one ink layer. It can by measuring the thickness of the ink layer be assessed whether it has sufficient coverage. It can therewith also be assessed whether the direct printing device has printed a sufficient amount of ink onto the container. The layer thickness measuring device can use a magnetic-inductive, an eddy current or an ultrasonic method for determining the ink layer thickness.

Holding devices can be provided with the device for inspecting a direct print for the purpose of receiving the containers in a fixed position. Units of the device for inspecting the direct print can thereby be arranged either upstream of the direct printing device as well as downstream thereof, where the exact position of the container relative to the individual units must be calibrated only once. The holding devices can be adapted to receive the container at the base and/or at the neck.

The invention further provides a method for correcting a direct print on containers with a relief-like surface contour, according to which the relief-like surface contour is at least partially printed onto with a direct printing device, characterized in that the direct print is following an inspection corrected by applying a correction print and/or by removing printing ink applied onto the container.

Due to the fact that applied printing ink can with the method be removed from containers, areas of the container can be corrected that were not to be printed onto but which were erroneously printed onto. Areas of the containers printed onto can also be corrected by use of the correction print, for example, if not enough printing ink was applied when printing with the direct printing device. Moreover, printing ink can in incorrectly printed areas first be removed and then a correction print is applied. Due to the correction, such inaccurately printed containers must not be discarded, but can be returned to the production cycle directly after correction.

The containers can be filled with beverages, hygiene products, pastes, chemical, biological and/or pharmaceutical products. The method can be applied, in particular, in a beverage processing plant. The containers can, in particular, comprise plastic bottles, glass bottles and/or cans. The method for correcting a direct print on containers with a relief-like surface contour can be provided for correcting a continuous flow of containers.

The relief-like surface contour can be a three-dimensional structure that stands out against a surrounding wall portion by elevations and/or depressions that are selectively and/or reproducibly creatable. Such relief-like surface contours preferably comprise contours at the macroscopic level, which can both be felt as well as seen by the human eye or spatially resolved at the viewing distances that are customary for the use or the sale of the containers.

The direct printing method can be an ink-jet printing process. Colors can in particular be used in the direct printing process which cure with heat or light, in particular UV-light. Curing of the printing ink can with the method be effected prior to or after correction printing.

The correction print can with the method be effected still in the same processing machine.

The correction print can with the method be applied with a separate correction printing device or the direct printing device onto the container. The correction printing device can be an ink-jet printing device. Inks can in particular be used in the direct printing process which cure with heat or light, in particular UV-light. The container can also again be transported to the direct printing device in order to therewith apply the correction print.

The direct print can with the method be cured in sections and non-cured sections can be corrected. The printing ink can there be cured only in those surface areas of the container in which the inspection delivers no detected errors. This can be effected by a controllable screen and/or rotation positioning of the container on a controllable rotary plate.

The printing ink can with this method be at least partially removed from the container by use of a solvent, in particular if errors were recognized during the inspection. This can be effected in particular by motor-driven adjustable nozzles which act upon the container with the solvent. Removal of the printing ink can be performed in particular in those surface areas in which the printing ink has not cured. This allows for the ink to easily come off the container. The printing ink can also be removed entirely from the container.

The invention further provides a device for performing a method for correcting a direct print on containers with a relief-like surface contour, according to which the device comprises a direct printing device for at least partial printing onto the relief-like surface contour, characterized in that the device comprises a correction device configured to correct the direct print following an inspection. Due to the fact that the device comprises a correction device, the containers, after being printed onto, can be corrected with the direct printing device in terms of the direct print and must not be recycled as scrap or be discarded. It is instead possible with the correction device to correct an inaccurate print such that the quality of the direct print complies with the quality requirements. The value of the container and therefore the product contained therein is thereby not reduced by inaccurate printing.

The correction device can be the direct printing device, a correction printing device, and/or a device for removing the printing ink applied onto the container. It is thereby possible to remove the direct print partially or entirely from the container and/or to apply additional printing ink onto the container. For example, non-intentional color splashes can be removed from a transparent container or with a non-transparent container be overprinted with the container color. Areas can also be overprinted which exhibit no sufficient ink coverage. The direct printing device and/or the correction printing device can be configured to apply a correction print. The device for removing printing ink applied onto the container can comprise nozzles which are configured for applying solvent onto the container. The nozzles can be adjustable by motor.

The device can comprise a transport diverter. The transport diverter can be configured to change over a container flow between two transport paths. The change-over can in particular depend upon the outcome of the inspection. A container with insufficient print quality can thereby be discharged from a normal flow of containers and be passed along the correction device. The normal flow of containers is thereby not interrupted during correction of a container A container with insufficient print quality can alternatively be discharged by the transport diverter from the normal flow of containers and returned to the direct printing device for application of the correction print. A container can in particular after correction be again reintroduced into the normal flow of containers by a further transport diverter. The transport diverter can be an actuateable distributor star.

The device can comprise a carousel having an odd number of container holders. In particular, only every second container holder can be loaded with a container at the inlet of the carousel and the containers from only every other second container holder can be removed at an outlet of the carousel. In particular a first transport path in the carousel can downstream of the inlet overlap with a second transport path in the carousel upstream of the outlet. It is thereby possible to have a container pass the overlap region twice. In the overlap region, a container can be printed onto when passing the direct printing device for the first time, and can be corrected or cured when passing the same direct printing device for the second time. Inspection of the direct print can also occur when passing for the first time, the second time or therebetween.

BRIEF DESCRIPTION OF THE SEVERAL VIEWS OF THE DRAWINGS

Further features and advantages of the invention shall be explained below with reference to embodiments illustrated in the Figures, in which:

FIG. 1 shows a flow diagram of a method 20 according to the invention for inspecting the direct print 2 on containers 1 with a relief-like surface contour 3. The method 20 is described in connection with the container 1 shown in FIG. 2 and the device according to the invention described in FIG. 3, but is not restricted thereto.

Figure 1:
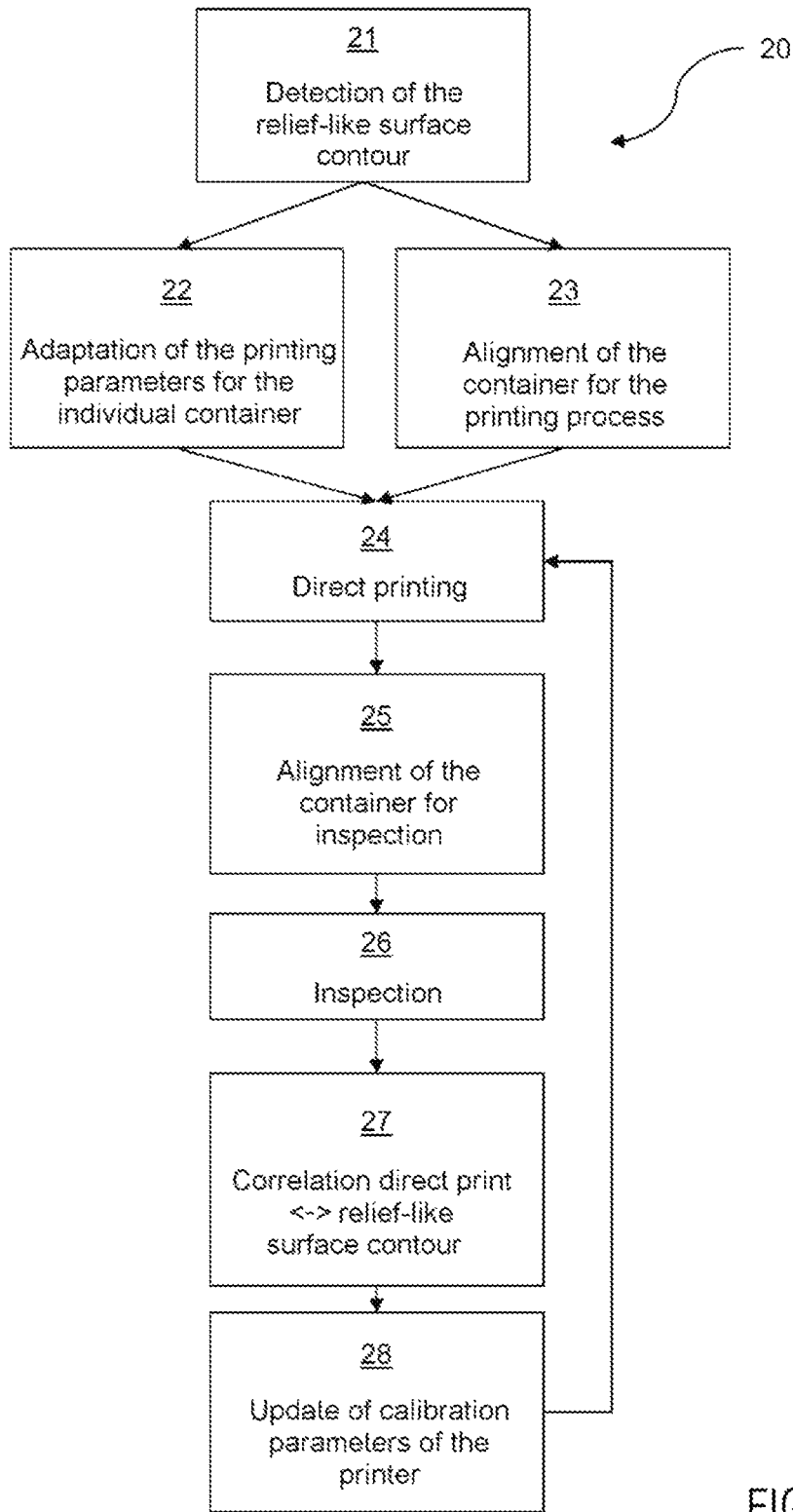
FIG. 1 shows a flow diagram of a method according to the invention for inspecting the direct print on containers with a relief-like surface contour.

The method 20 first starts with process step 21 for detection of the relief-like surface contour 3. The measuring method is explained below in more detail in the description of FIG. 3. With a detection unit 4, respective contour characteristics of the relief-like surface contour 3 can there be detected, where, firstly, the exact position of the container 1 can be detected as well as the actual shape of the relief-like surface contour 3.

In a further process step 22, printing parameters of a direct printing device 5 can be adjusted for every container 1 with the results of process step 21. It is thereby much better possible to realize an accurate direct print since deviations from the target shape of the relief-like surface contour 3 can be incorporated when printing.

Parallel to that, the containers 1 can in a process step 23 be aligned for the printing process 24. The containers 1 are there fitted with holding devices in which the container mounts are firmly received. The containers 1 therefore do not lose their orientation relative to the direct printing device 5 and the inspection device 4, 6, 9.

In process step 24, the containers 1 are provided with a direct print 2 being composed of five colors. The containers are there sequentially printed onto with the colors cyan, magenta, yellow, black and white. The print heads $5_C$, $5_M$, $5_Y$, $5_S$, $5_W$ there operate according to the ink-jet principle. The colors can be quickly cured and without running by use of UV-lamps 8. The container 1 therefore comprises a direct print 2 on the relief-like surface contour 3.

Since the containers 1 are connected to holding devices in a fixed position, rotation and thus alignment of the container 1 for inspection occurs in process step 25. If the containers 1 are not fixedly connected to holding devices, then they can be alternatively aligned with the aid of a camera by capturing defined contour characteristics.

During inspection 26, each container 1 is guided past a camera system with which the container 1 is illuminated with light as uniform as possible, and the direct print is thus captured in an image. Respective printing characteristics of the direct print 2 are subsequently analyzed and detected with a calculation method. These printing characteristics are in a further process step 27 correlated with the contour characteristics of the relief-like surface contour 3. It can then be decided in an assessment process, whether the quality and/or the position of the direct print 2 applied on the relief-like surface contour 3 corresponds to a predetermined quality standard.

If the quality and/or the position of the applied direct print 2 is below the predetermined standards, then the respective container can be sorted out and the calibration parameters of the printing device 5 can additionally with process step 28 be adapted such that subsequent containers 1 are printed onto correctly. Servicing and/or cleaning the printing device 5 can also be initiated.

It is with the method illustrated in FIG. 1 therefore possible to calculationally assess the quality of the direct print 2 and its position on the relief-like surface contour 3 and to further process only those containers 1 that do not fail the quality standard. It is thereby prevented that the value of the containers is reduced.

Figure 2:
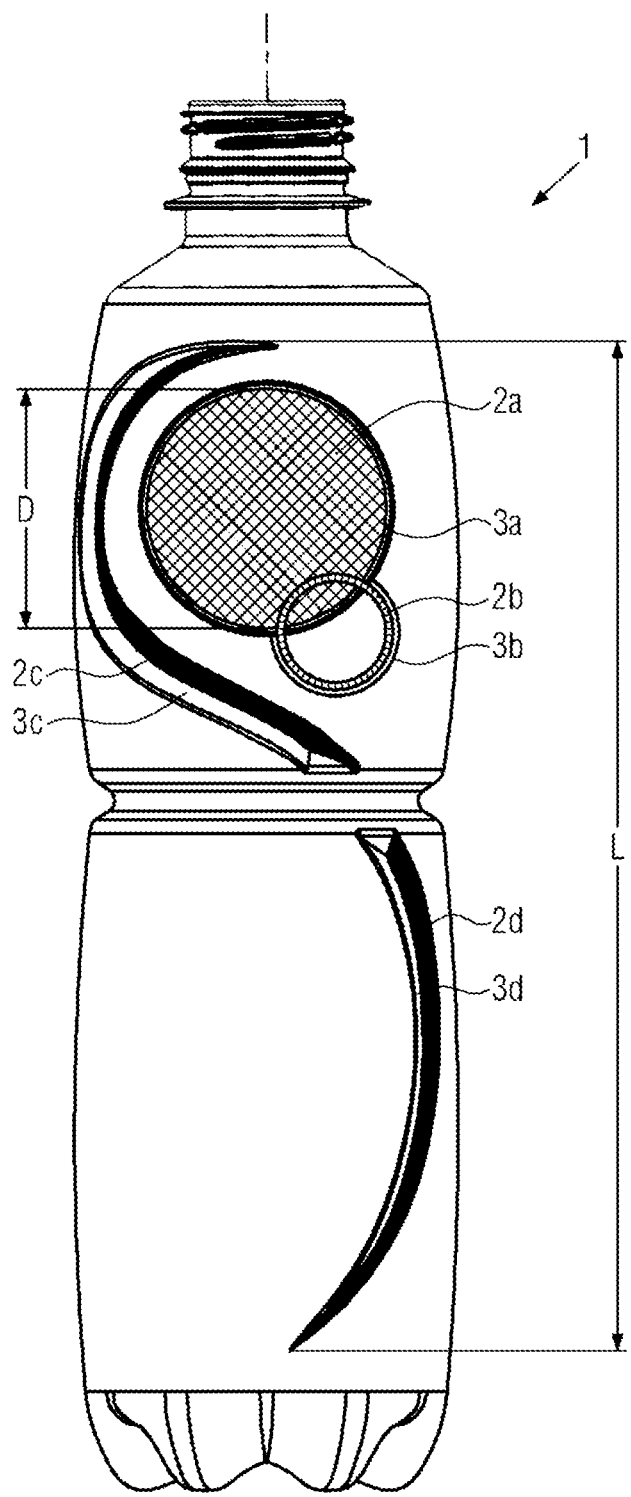
FIG. 2 shows an representation of an exemplary container which is inspected using the method according to the invention of FIG. 1.

FIG. 2 shows a representation of an exemplary container which is inspected by the method according to the invention of FIG. 1.

A container 1 made of transparent plastic is shown, such as PET, and has a cylindrical basic shape with a waist. In addition, the container 1 comprises various areas having various relief-like surface contours 3a-3d. It is there evident that the entire relief-like surface contour 3a and 3b is in the areas 2a and 2b printed onto with ink, where the direct print 2a and 2b each have a different printing color. In the areas 3c and 3d of the surface contour, only one side of the indentation is printed onto with a direct print 2c and 2d with one color.

The characteristic lengths L and D are also shown in FIG. 2 which can be used both as printing characteristics as well as contour characteristics.

Figure 3:
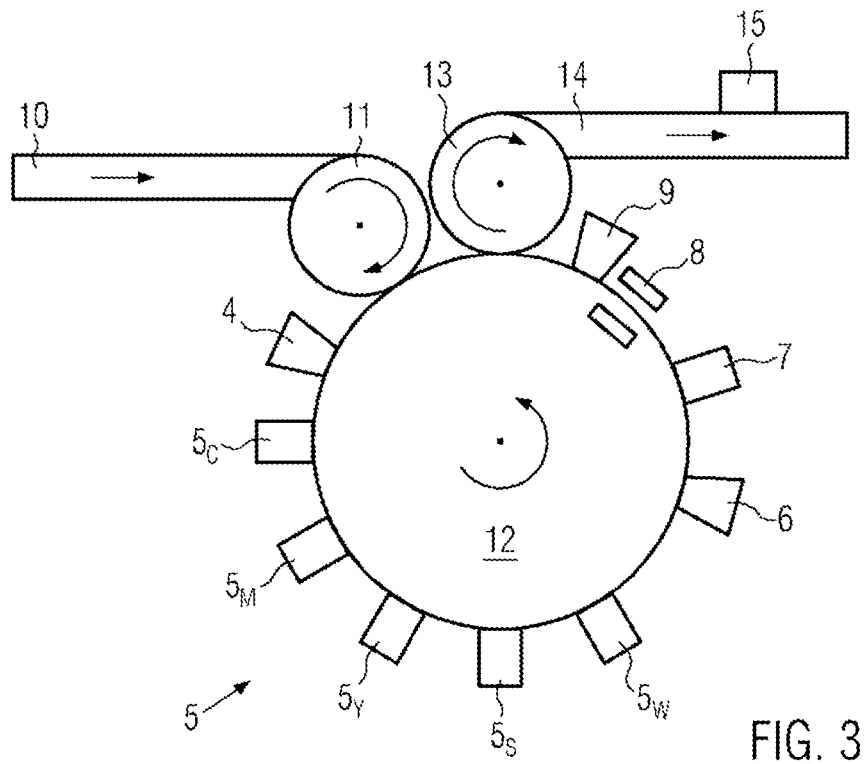
FIG. 3 shows a representation of a device according to the invention for inspecting or correcting the direct print on containers with a relief-like surface contour in plan view.

FIG. 3 shows a representation of a device according to the invention for inspecting or correcting the direct print 2 on containers 1 with a relief-like surface contour 3 in plan view. A feeder 10 can be seen with which the container 1 (presently not shown) is via a deflection star 11 fed to a carousel 12. The containers 1 are there during transport in the carousel 12 provided with a direct print 2 and inspected with an inspection device 4, 6, 9. The containers 1 are then via a deflection star 13 and a discharge 14 supplied to other processing stations (presently not shown). An ejector 15 is located in the region of discharge 14 to remove the containers 1 with reduced quality from processing or for returning them to the same machine 5 for correction printing or reprinting. The printing device operates in particular cyclically, but it is also conceivable to let it operate continuously, where the print heads at least in sections accompany the container.

The containers 1 are first downstream of the deflection star 11 in the carousel 12 received by holding devices (presently not shown) in a fixed position. The containers 1 can therefore be located only in defined positions relative to the carousel 12. The holding devices are there designed such that they can rotate about their own axis with the containers 1 to enable printing along the full container circumference and a respective inspection. The containers 1 are there guided past a detection unit 4 for relief-like surface contours 3. An illuminated screen is there located within the detection unit 4 with stripe-like structures that are oriented along the container axis. The light pattern is reflected by a light reflection from the container surface and is captured by a camera. The container 1 and the light reflection are therefore visible in the camera image with a respectively distorted striped pattern. The striped pattern is distorted firstly by the cylindrical basic shape of the container surface and secondly by the relief-like surface contour 3. The reflected light pattern is especially greatly distorted at the edges of the relief-like surface contour 3. The exact position of the container 1 relative to the holding device as well as errors in the relief-like surface contour 3 can therefore be determined with the detection unit 4.

The data obtained from the detection unit 4 is passed on to the printing device 5 in order to achieve the most accurate print of the container 1. In the printing device 5, the color cyan is first printed onto the container 1 by print head $5_C$ and the colors magenta, yellow, black and white by the subsequent print heads $5_M$, $5_Y$, $5_S$, $5_W$. The printing device 5 is based on the ink-jet principle.

The inspection device comprises a camera 6 with which a color image of the direct print 2 is captured after the printing operation. The contour characteristics of the relief-like surface contour 3 are by correlation superimposed by the color image of the direct print 2. Precise analysis of the printing characteristics of the direct print 2 with respect to the relief-like surface contour 3 is thereby possible. Respective threshold values are there used to assess the quality and/or the position of the direct print 2 on the relief-like surface contour 3. The assessment leads, firstly, to recalibration of the printing parameters and, secondly, to a decision as to whether the respective container 1 is to receive a correction print in the correction printing device 7 or whether it is in the later course ejected in the ejector 15. The correction printing device 7 comprises print nozzles with all colors.

In the further course of the carousel 12, the inks are cured with a UV-lamp 8, in particular where the quality and position of the direct print 2 comply with the quality standard. This has the advantage that the inks can not run due to a lengthy drying procedure. The overall print result is then again inspected in the unit 9 of the inspection device in terms of its quality and/or position. Unit 9, like unit 6, comprises a camera for assessment of the print image. A correlation of the direct print 2 with the relief-like surface contour 3 is also performed.

FIG. 3 also shows that the inspection device comprises the detection unit 4 for relief-like surface contours 3, the first inspection unit 6, and the second inspection unit 9 and that they can be arranged separated from each other. The inspection unit can comprise multiple detection units 4 for relief-like surface contours 3 and multiple inspection units 6, 9. They can be arranged both upstream as well as downstream of the printing device.

Figure 4:
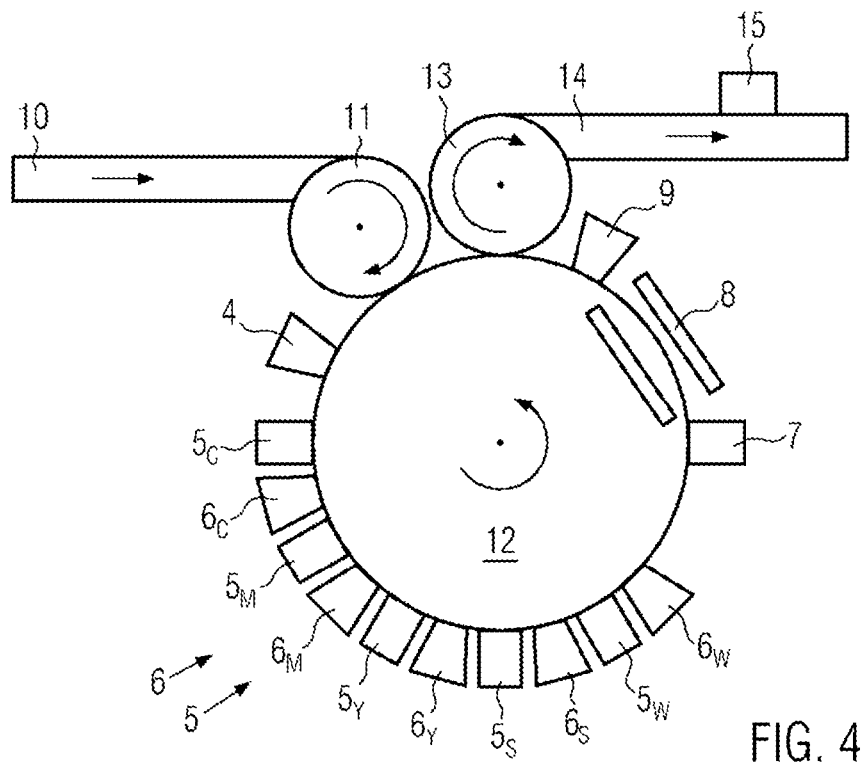
FIG. 4 shows a representation of a further device according to the invention in plan view.

FIG. 4 shows a further embodiment according to the invention of a device for inspecting or correcting a direct print 2 on containers 1 with a relief-like surface contour 3 in plan view. The device shown in FIG. 4 differs from that shown in FIG. 3 in that an inspection is performed with the inspection units $6_C$, $6_M$, $6_Y$, $6_S$ between the respective print heads $5_C$, $5_M$, $5_Y$, $5_S$, $5_W$. A first printing result of all colors is inspected by inspection unit $6_W$.

In the device shown in FIG. 4, an image of the direct print 2 is captured by the inspection units $6_C$, $6_M$, $6_Y$, $6_S$, $6_W$ immediately after printing each color. Each camera image is evaluated in terms of quality and location of each color of the direct print 2 on the relief-like surface contour 3.

It is by use of decision criteria thereby possible, after printing each printing ink, to assess whether the container 1 is released for printing further colors, or whether possibly a correction print with the correction printing device 7 must occur, or whether the container is at the ejector 15 supplied to the discharge. Printing ink can therefore be reduced with this method.

Figure 5:
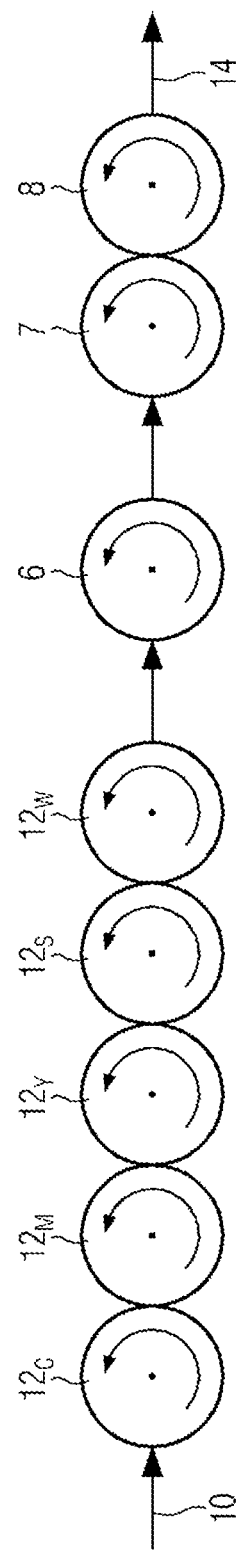
FIG. 5 shows a representation of a further device according to the invention in plan view.

FIG. 5 shows a further embodiment according to the invention of a device for inspecting or correcting a direct print 2 on containers 1 with a relief-like surface contour 3 in plan view. The device in FIG. 5 there differs from that in FIG. 3 in that the print heads for the various colors are each disposed in separate carousels $12_C$, $12_M$, $12_Y$, $12_S$, $12_W$ and that the inspection device 6, the correction printing device 7, and the curing device 8 are additionally disposed in separate carousels.

The containers 1 (presently not shown) are there first via a feeder 10 supplied to the first print carousel $12_C$ and printed onto with the color cyan. In the other carousels $12_M$, $12_Y$, $12_S$, $12_W$, the containers 1 are subsequently printed onto with the colors magenta, yellow, black and white. The containers are in the inspection device 6 also in a carousel guided past a laser triangulation unit with which the relief-like surface contour 3 is measured as 3D-coordinates. In addition, a camera is installed therein with which the printing characteristics of the direct print 2 can be captured. They are then correlated with the 3D-coordinates of the relief-like surface contour 3 such that the direct print 2 can be assessed in terms of its quality and position on the 3D-surface contour 3. The containers 1 is then optionally provided with a correction print in the correction printing device 7 designed as a carousel. In the downstream carousel 8, the colors are cured with UV-light.

Figures 6A, 6B:
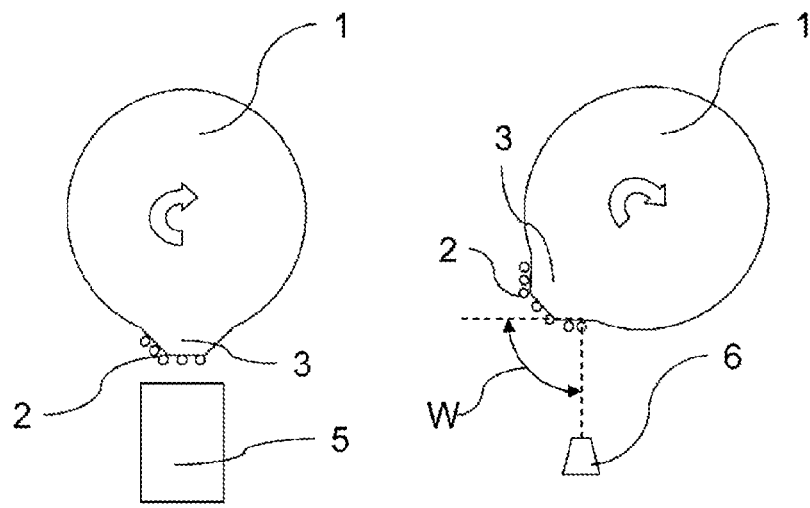
FIG. 6a shows a representation of the orientation of a printing device relative to the container in plan view.
FIG. 6b shows a representation of the container of FIG. 6a rotated relative to the inspection device with the direct print, as a result of the rotation of the container, in a most vertical position as possible in front of the inspection device.

FIGS. 6a-6b show a representation of the orientation of the (stationary) printing device 5 and the inspection device 6 relative to the container 1 in plan view. FIG. 6a shows a container 1 in plan view comprising a relief-like surface contour 3. The direct printing device 5 is there arranged in a rotationally fixed manner relative to the container 1. The container is then with a clockwise rotation applied the direct print 2. If the clock frequency of the ink ejection of the ink dots 2 and the rotation speed of the container 1 about the circumference of the container 1 remain constant, then the resolution of the surface contour 3 would be different than the resolution of the rest of the circumference. The container must for this reason be rotated relative to the printing device subject to a certain rotation-time profile. The container 1 is then with a rotation guided past the inspection device 6 in order to inspect the position and the quality of the direct print 2 on the relief-like surface contour 3. It can be seen in FIG. 6b that the direct print 2 is due to the rotation of the container 1 in a most vertical position as possible located in front of the inspection device 6. The viewing angle W of the inspection device 6 should there on the respective area of the surface contour 3 best be 90°.

Figures 7A, 7B, 7C:
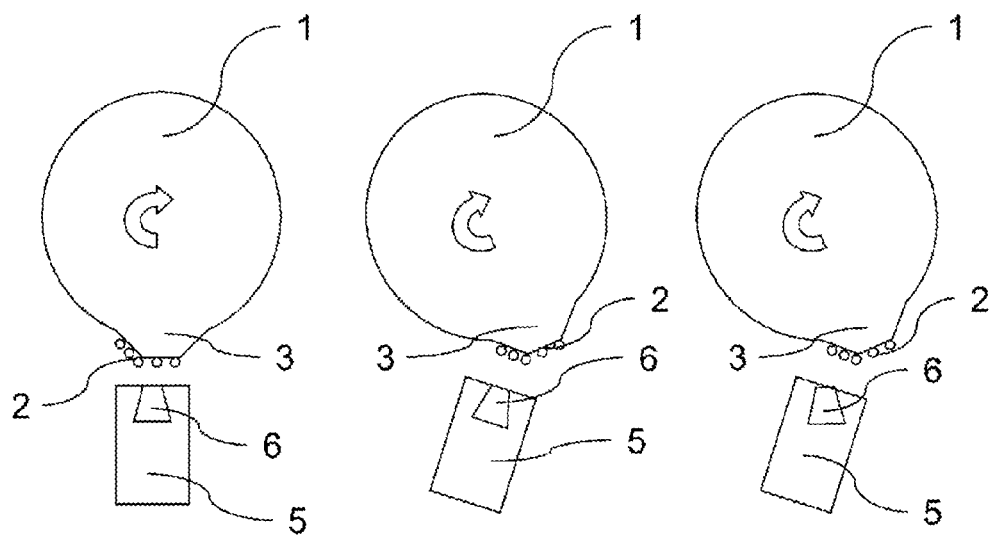
FIG. 7a shows a further orientation of a direct printing and inspection device relative to the container in plan view.
FIG. 7b shows yet a further orientation of a direct printing and inspection device relative to the container in plan view.
FIG. 7c shows seven yet a further orientation of a direct printing and inspection device relative to the container in plan view.

FIGS. 7a-7c show representations of further orientations of the direct printing device 5 and the inspection device 6 relative to the container 1 in plan view. It is there evident that a better print or inspection result can be achieved by pivoting the printing device 5 and/or the inspection device 6.

The printing device 5 and the inspection device 6 are in FIG. 7a disposed in a fixed position relative to the container. Individual areas of the surface contour 3 can thereby be printed onto only from a slanted angle. Inspection by the inspection device 8 in unfavorable areas of the surface contour 3 likewise occurs from a slanted angle. This can be improved, as shown in FIG. 7b, in that the direct printing device 5 and the inspection device 6 are pivotably arranged. A better printing result is then obtained due to the vertical impact of the printing ink on the relief-like surface contour 3. A better inspection result can thereby likewise be obtained in areas with steep edges of the surface contour 3.

Furthermore, as shown in FIG. 7c, only the printing device 5 can be pivotably arranged and the inspection device 6 can be fixedly arranged. An inexpensive embodiment of the inspection device can result therefrom. Furthermore, the printing device 5 can be fixedly arranged and the inspection device 6 can be pivotable.

The print head 5 according to FIGS. 7a-7c can also be a correction printing device 7.

Figure 8:
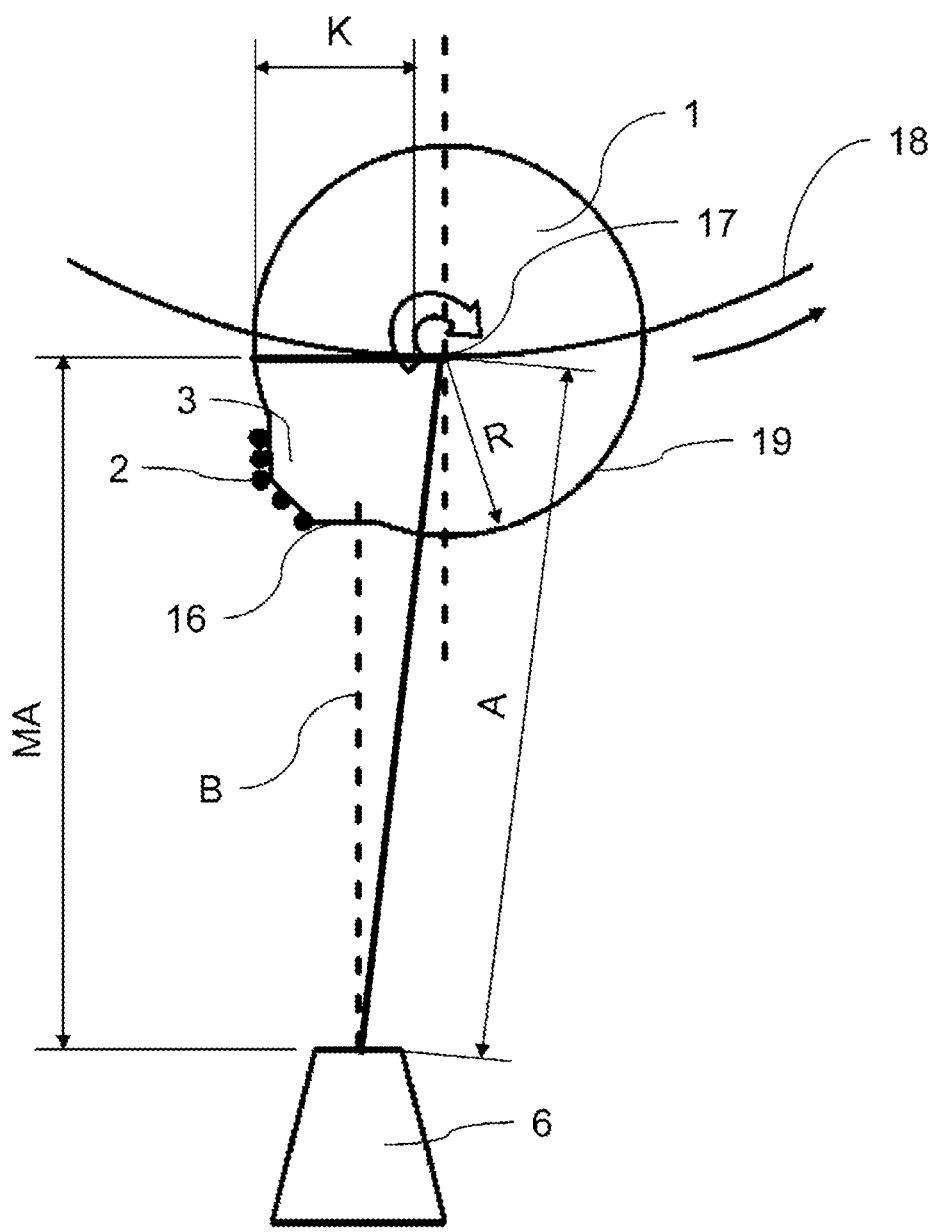
FIG. 8 shows a representation of the orientation of the inspection device with respect to the relief-like surface contour in plan view.

FIG. 8 shows a representation of the orientation of the inspection device 6 with respect to the relief-like surface contour 3 in a plan view. A container 1 is shown which is passed along a transport path 18 past the inspection device 6.

The container 1 is there by rotation about its own axis oriented such that the partial surface 16 of the relief-like surface contour 3 at the moment of inspection is aligned perpendicular to the axis of inspection B. The partial surface 16 has a tangent extending slanted to the container basic shape 19. With this alignment of the axis of inspection B to the partial surface 16, a more reliable inspection result can be obtained for this area. The container 1 can for different partial surfaces 16 be aligned differently during the inspection process.

The inspection therefore occurs at a moment at which the axis of inspection intersects the inspection area K. In other words, the distance A between the center 17 of the container and the inspection device 6 during the inspection is in a range of $$\sqrt{\left(\frac{R}{4}\right)^2 + MA^2} \le A \le \sqrt{R^2 + MA^2}.$$

Figure 9:
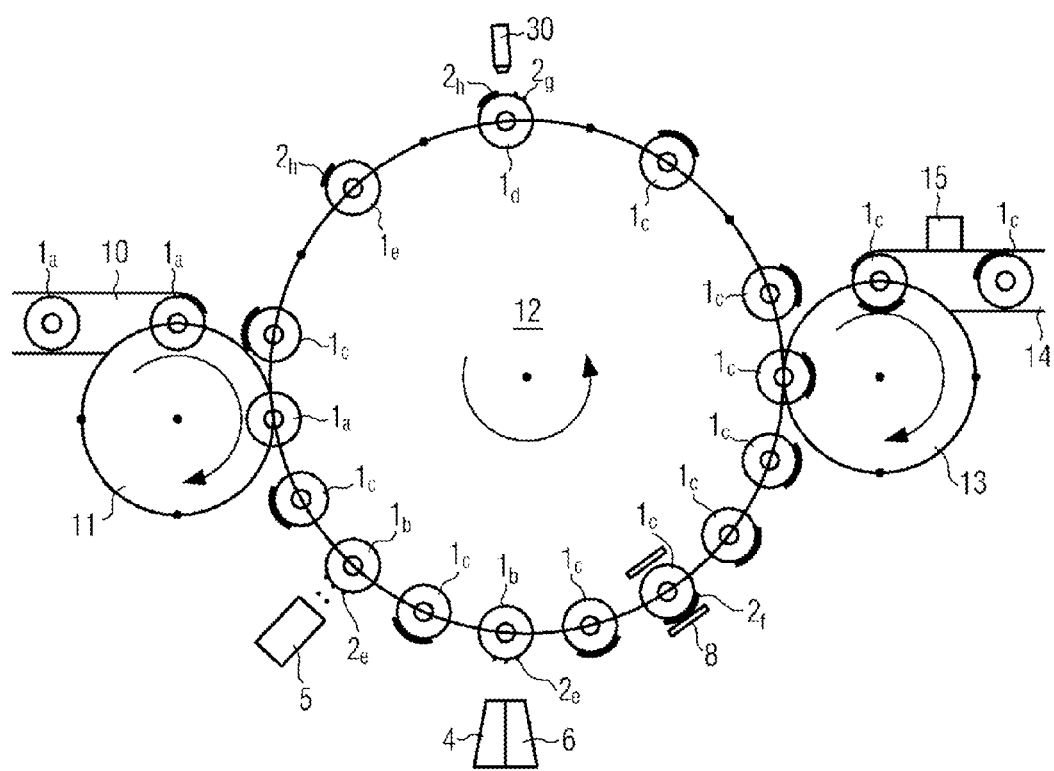
FIG. 9 shows a representation of a device according to the invention for inspecting or correcting a direct print on containers with a relief-like surface contour in plan view.

FIG. 9 shows a representation of a device according to the invention for inspecting or correcting a direct print 2 on containers 1 with a relief-like surface contour 3 in plan view. It shows a device in which the containers are printed onto in a carousel 12 with the direct printing device 5 and inspected by the inspection device 4, 6. At least partial areas of the direct print 2g, 2h of a container 1d can in the device be cured with a UV-lamp or, alternatively, be removed with a device for removing printing ink 30. The direct print with insufficient print quality 2h on the container 1e is then reprinted by the direct printing device 5 in the same carousel 12 and again inspected by the inspection device 4, 6 and cured by the UV-lamp 8. The correctly printed containers 1c are then via a deflection star supplied to further processing stations (presently not shown).

The containers 1a are first downstream of the deflection star 11 in the carousel 12 received by holding devices (presently not shown) in a fixed position. The deflection star 11 there fills only every second holding device of the carousel 12 with a container 1a, where the carousel comprises an odd number of holding devices.

The colors cyan, magenta, yellow, black and white are in the printing device 5 applied with print heads as a direct print 2e onto the containers 1b. The direct print 2e is there not yet cured and therefore is initially still removable from the container. The printing device 5 is based on the ink-jet principle.

The containers 1a are subsequently guided past a detection unit 4 for relief-like surface contours 3. An illuminated screen is there located within the detection unit 4 with stripe-like structures that are oriented along the axis of the container. The light pattern is reflected by a light reflection at the container surface and is captured by a camera. The container 1b and the light reflection are therefore visible in the camera image with a respectively distorted striped pattern. The striped pattern is distorted firstly by the cylindrical basic shape of the container surface and secondly by the relief-like surface contour 3. The reflected light pattern is in particular greatly distorted at the edges of relief-like surface contour 3. The exact position of the container 1 relative to the holding device as well as errors in the relief-like surface contour 3 can therefore be determined with the detection unit 4.

The non-cured direct print 2e is then inspected by the inspection device 6. The inspection device comprises a camera 6 with which a color image of the direct print 2e is captured after the printing operation. The contour characteristics of the relief-like surface contour 3 are by correlation superimposed with the color image of the non-cured direct print 2e. Precise analysis of the printing characteristics of the direct print 2e with respect to the relief-like surface contour 3 is thereby possible. Appropriate threshold values are there used to assess the quality and/or the position of the direct print 2e on the relief-like surface contour 3. This assessment leads, firstly, to recalibration of the printing parameters and, secondly, to a decision as to whether ink is to be removed from the respective container 1b and/or a correction print is to occur when passing through the direct printing device 5 for the second time, or whether it is in the later course ejected at the ejector 15.

In the further course of the carousel 12, the colors are cured with a UV-lamp 8 if the quality and the position of the direct print 2e comply with the quality standard. The UV-lamp 8 is configured such that it cures the entire direct print 2f on a container 1c properly printed onto.

When a container 1d, however, exhibits a correct direct print 2h only in a partial area, then this area is also cured. This is done by the arrangement of respective apertures (presently not shown) in front of the UV-lamp 8. The partial area of the direct print 2g not correctly printed onto is there not cured and subsequently removed with a device 30 for removing the printing ink applied. A solvent is sprayed with nozzles onto the faulty direct print 2g. The container 1e is then dried (presently not shown) and only in a partial area exhibits a proper direct print 2h.

When passing the direct printing device 5 for the second time, the faulty printed container 1e is respectively printed onto correctly, inspected by the inspection device 4, 6, and cured with the UV-lamp 8.

The deflection star 13 removes every second container from the carousel 12 once the latter has passed the direct printing device 5 for the second time and transports it to the outlet 14. It is alternatively conceivable that the deflection star 13 in dependence of the print result removes the containers 1c printed onto correctly from the carousel immediately after they have passed for the first time and leaves only those containers 1d, 1e at the direct printing device in the carousel that have not been printed onto correctly. If the direct print 2 of a container 1d, 1e, cannot be corrected, then it is ejected by the ejector 15 and subsequently recycled or discarded.

The device of the invention according to FIG. 9 has the advantage that the same direct printing device 5 can be used for applying the correction print as for the actual direct print 2e. Therefore, the system is less costly. In addition, the container discard can with the device shown in FIG. 9 be reduced to a minimum due to the removal of the incorrect direct print 2g, which likewise results in respective cost advantages since the respective containers are merely reprinted and not recycled.

It is understood that the features previously mentioned in the embodiments described are not restricted to these specific combinations and are also possible in any other combinations.

The invention claimed is:

1. A method for inspecting a direct print on a container with a relief-like surface contour, wherein said direct print is at least partially printed onto said relief-like surface contour, the method comprising:
   detecting, in a first step, using an inspection device, actual contour characteristics of said relief-like surface contour, the actual contour characteristics comprising a three-dimensional contour/shape of said relief-like surface contour;
   detecting, in a second step, using the inspection device, actual printing characteristics of said direct print on said container; and
   matching, using the inspection device, the actual contour characteristics with the actual printing characteristics;
   wherein matching the actual contour characteristics with the actual printing characteristics comprises superimposing, using the inspection device, one of the actual contour characteristics and the actual printing characteristics onto the other of the actual contour characteristics and the actual printing characteristics; and
   wherein said direct print is, in terms of its quality and/or position relative to the actual contour characteristics, inspected with said inspection device.

2. The method for inspecting a direct print on a container according to claim 1, wherein said containers are, prior to printing, attached in a fixed position to holding devices, wherein said contour characteristics of said relief-like surface contour are detected prior to printing and said printing characteristics are detected after printing.

3. The method for inspecting a direct print on a container according to claim 1, said direct print being, after inspection, corrected with a correction print.

4. The method for inspecting a direct print on a container according to claim 1, and transmitting a correction signal for calibrating said direct print from said inspection device to a direct printing device.

5. The method for inspecting a direct print on a container according to claim 1, and said direct print is performed sequentially by print heads with different printing inks, and inspecting at least one of an intermediate result of said direct print between at least two print heads, or the overall result after printing all printing inks.

6. The method for inspecting a direct print on a container according to claim 1, wherein partial surfaces of said relief-like surface contour with a tangent that is slanted relative to the basic shape of said container are aligned perpendicular to an inspection axis.

7. A method for correcting a direct print on containers with a relief-like surface contour, wherein said direct print is at least partially printed onto said relief-like surface contour with a direct printing device, the method comprising: following an inspection of the direct print with the method for inspecting a direct print on a container according to claim 1, correcting the direct print by applying a correction print onto said container.

8. The method for correcting a direct print according to claim 7, wherein said correction print is applied with a separate correction printing device or said direct printing device onto said container.

9. The method for correcting a direct print according to claim 7, wherein said direct print is cured in sections and non-cured sections are corrected.

10. The method for correcting a direct print according to claim 7, further comprising removing at least a portion of said direct print on said container when the inspection determines that an error has been made.

11. A device for inspecting a direct print on a container with a relief-like surface contour, the device comprising:
   a direct printing device for at least partially printing said direct print onto said relief-like surface contour;
   at least one camera for detecting actual printing characteristics of said direct print on said container;
   at least one of a detection unit for relief-like surface contours, a camera, or a triangulation unit for detecting actual contour characteristics of said relief-like surface contour, the actual contour characteristics comprising a three-dimensional contour/shape of said relief-like surface contour; and
   at least one inspection device for inspecting said direct print in terms of at least one of its quality and position relative to the actual contour characteristics by matching the actual printing characteristics with the actual contour characteristics, wherein matching the actual contour characteristics with the actual printing characteristics comprises superimposing, using the inspection device, one of the actual contour characteristics and the actual printing characteristics onto the other of the actual contour characteristics and the actual printing characteristics.

12. The device for inspecting a direct print according to claim 8, where said at least one camera detects printing characteristics of said direct print and said contour characteristics of said relief-like surface contour.

13. The device for inspecting a direct print according to claim 11, where at least one of said containers, said direct printing device, or said at least one inspection device is pivotably arranged.

14. The device for inspecting a direct print according to claim 11, where said at least one inspection device comprises at least one layer thickness measuring device which measures the thickness of at least one ink layer.

15. The device for inspecting a direct print according to claim 11, wherein holding devices are provided to receive said containers in a fixed position.

16. A device for inspecting a direct print on a container with a relief-like surface contour according to claim 11, further comprising a correction device configured to correct said direct print following an inspection of the direct print.

17. The device for inspecting a direct print on a container with a relief-like surface contour according to claim 16, further comprising a device for removing printing ink applied onto said container.

18. The device for inspecting a direct print on a container with a relief-like surface contour according to claim 16, where said device comprises a transport diverter.

19. The device for inspecting a direct print on a container with a relief-like surface contour according to claim 16, where said device comprises a carousel having an odd number of container holders.

* * * * *